United States Patent
Su et al.

(10) Patent No.: US 9,184,607 B2
(45) Date of Patent: Nov. 10, 2015

(54) BATTERY MODULE AND OVERCHARGE PROTECTING METHOD THEREOF

(71) Applicants: Yu-Hsiu Su, Taipei (TW); Ke-Jen Hung, Taipei (TW); Yu-Cheng Shen, Taipei (TW)

(72) Inventors: Yu-Hsiu Su, Taipei (TW); Ke-Jen Hung, Taipei (TW); Yu-Cheng Shen, Taipei (TW)

(73) Assignee: ASUSTek COMPUTER INC., Taipei (TW)

( * ) Notice: Subject to any disclaimer, the term of this patent is extended or adjusted under 35 U.S.C. 154(b) by 130 days.

(21) Appl. No.: 14/185,893

(22) Filed: Feb. 20, 2014

(65) Prior Publication Data
US 2014/0253042 A1 Sep. 11, 2014

Related U.S. Application Data

(60) Provisional application No. 61/774,601, filed on Mar. 8, 2013.

(30) Foreign Application Priority Data

Dec. 17, 2013 (CN) .......................... 2013 1 0695357

(51) Int. Cl.
| | |
|---|---|
| *H02J 7/00* | (2006.01) |
| *H01M 10/00* | (2006.01) |
| *G08B 21/00* | (2006.01) |
| *G01N 27/416* | (2006.01) |
| *H01M 10/42* | (2006.01) |

(52) U.S. Cl.
CPC ............ *H02J 7/0029* (2013.01); *H01M 10/425* (2013.01); *H01M 10/4207* (2013.01); *H02J 7/0031* (2013.01); *G01N 27/416* (2013.01); *G08B 21/00* (2013.01); *H02J 2007/0037* (2013.01)

(58) Field of Classification Search
CPC .................. H02J 7/0029; H02J 7/0031; H02J 2007/0037; H01M 10/4207; H01M 10/425; G08B 21/00; G01N 27/416
USPC .......................... 320/134, 149, 162; 324/433; 340/636.15, 636.17
See application file for complete search history.

(56) References Cited

U.S. PATENT DOCUMENTS

| | | | | |
|---|---|---|---|---|
| 5,640,080 A | * | 6/1997 | Tamai | ................... H01M 10/44 320/141 |
| 5,808,446 A | * | 9/1998 | Eguchi | .................. H02J 7/0093 320/134 |

(Continued)

FOREIGN PATENT DOCUMENTS

| | | |
|---|---|---|
| CN | 101355185 | 1/2009 |
| CN | 102148410 | 8/2011 |

*Primary Examiner* — Phallaka Kik
(74) *Attorney, Agent, or Firm* — Jianq Chyun IP Office

(57) ABSTRACT

A battery module and an overcharge protecting method are provided. The overcharge protecting method includes following steps: detecting a battery voltage of a rechargeable battery during a charging process; determining whether the battery voltage is larger than or equals to an upper limit voltage; if no, continuously charging the rechargeable battery until the battery voltage reaches a charging cut-off voltage and then the charging process is ended; if yes, stopping the charging process, reducing the value of the charging cut-off voltage and using the reduced charging cut-off voltage as the charging cut-off voltage in the next charging process. In the subsequent charging process, once the overcharge occurs, the value of the charging cut-off voltage is continuously reduced until the overcharge of the rechargeable battery does not occur during the charging process.

12 Claims, 4 Drawing Sheets

(56) References Cited

U.S. PATENT DOCUMENTS

| | | | | |
|---|---|---|---|---|
| 5,994,878 A * | 11/1999 | Ostergaard | H02J 7/0004 | 320/132 |
| 2003/0071599 A1* | 4/2003 | Yoo | G01R 31/36 | 320/132 |
| 2005/0156574 A1* | 7/2005 | Sato | H02H 7/18 | 320/134 |
| 2009/0153100 A1* | 6/2009 | Okumura | H02J 7/0026 | 320/116 |
| 2010/0097033 A1* | 4/2010 | Tange | H02J 7/0026 | 320/116 |
| 2011/0001352 A1* | 1/2011 | Tamura | B60R 16/033 | 307/9.1 |
| 2011/0006733 A1* | 1/2011 | Tatebayashi | H01M 10/441 | 320/116 |
| 2011/0133571 A1* | 6/2011 | Kiyohara | H01M 10/44 | 307/130 |
| 2011/0287283 A1* | 11/2011 | Liu | H02J 7/0031 | 429/7 |
| 2012/0001595 A1* | 1/2012 | Maruyama | H02J 7/0016 | 320/118 |
| 2012/0133329 A1* | 5/2012 | Yoshida | H01M 10/441 | 320/116 |
| 2013/0069598 A1* | 3/2013 | Tanaka | H01M 10/0525 | 320/134 |
| 2013/0187466 A1* | 7/2013 | Sakai | G01R 19/16542 | 307/52 |
| 2014/0253041 A1* | 9/2014 | Takeda | H01M 10/44 | 320/134 |
| 2014/0312831 A1* | 10/2014 | Lewis | B60L 11/1822 | 320/107 |

* cited by examiner

BATTERY MODULE AND OVERCHARGE PROTECTING METHOD THEREOF

CROSS-REFERENCE TO RELATED APPLICATION

This application claims the priority benefits of U.S. provisional application Ser. No. 61/774,601, filed on Mar. 8, 2013, and China application serial No. 201310695357.1, filed on Dec. 17, 2013. The entirety of each of the above-mentioned patent applications is hereby incorporated by references herein and made a part of specification.

BACKGROUND OF THE INVENTION

1. Field of the Invention

The invention relates to a charging protection method for a rechargeable battery and, more particularly, to a battery module and an overcharge protecting method.

2. Description of the Related Art

In a conventional portable electronic device, a high capacity lithium battery without memory effect is usually used as a built-in rechargeable battery. When the lithium battery is used in an electronic product, a plurality of lithium battery units are usually connected in series to provide a voltage to the electronic product. For example, in a notebook computer, three or four lithium battery units are connected in series to form a rechargeable lithium battery and provide an 11.1V or 14.8V battery voltage. However, since the voltage and electrical characteristic of each battery are different, the voltage and capacity of each battery unit are different. After several cycles of charge-discharge, the difference would become more obvious (which means the rechargeable battery gradually degrades).

The effect of the degradation of the rechargeable battery is more obvious when a quick charger is used to charge the battery. In detail, the lithium battery is taken as an example, when the lithium battery is continuously charged with a large current, the lithium battery unit which degrades more seriously is easy to be charged to a too high battery voltage (that is overcharge). When the overcharge occurs, the material in a lithium ion cell of the lithium battery decomposes, which results in the increase of the resistance and the temperature, and then combustible gas is generated. Consequently, if the overcharge frequently occurs, the lithium battery may overheat, burn or even explode.

In conventional technology, a common overcharge protection mechanism is launched when the rechargeable battery reaches a specific voltage. The charging process is stopped to avoid the overcharge. However, the overcharge protection mechanism takes effect and protects the rechargeable battery only after the overcharge occurs, so it cannot stop or avoid the overcharge. If the overcharge of the rechargeable battery occurs frequently, its degradation speeds up, and the service life and reliability of the rechargeable battery are affected seriously.

BRIEF SUMMARY OF THE INVENTION

A battery module and an overcharge protecting method thereof which can effectively avoid an overcharge of a rechargeable battery are provided.

An overcharge protecting method for a rechargeable battery includes following steps: detecting a battery voltage of the rechargeable battery in a charging process; determining whether the battery voltage is larger than or equals to an upper limit voltage; if no, continuously charging the rechargeable battery until the battery voltage reaches a charging cut-off voltage and then the charging process is ended; if yes, stopping the charging process, reducing a value of the charging cut-off voltage and using the reduced charging cut-off voltage as the charging cut-off voltage in the next charging process.

A battery module which can be charged and discharge repeatedly includes a rechargeable battery and an overcharge protection device. The overcharge protection device includes a detecting unit and a processing unit. The detecting unit detects a battery voltage of the rechargeable battery in a charging process. The processing unit is coupled to the detecting unit. The processing unit determines whether the battery voltage is larger than or equals to an upper limit voltage in the charging process. When the processing unit determines the battery voltage is smaller than the upper limit voltage, the rechargeable battery is continuously charged until the battery voltage reaches a charging cut-off voltage and the charging process is ended. When the processing unit determines the battery voltage is larger than or equals to the upper limit voltage, the processing unit stops the charging process and reduces the value of the charging cut-off voltage, and the processing unit takes the reduced charging cut-off voltage as the charging cut-off voltage in the next charging process.

As stated above, a battery module and an overcharge protecting method are provided. The overcharge protecting method can dynamically adjust the charging cut-off voltage of the rechargeable battery when an overcharge of the rechargeable battery occurs. Thus, the rechargeable battery is charged based on a lower charging cut-off voltage in the next charging process, which can avoid shortening a service life of the rechargeable battery due to frequent overcharge. A battery burning or exploding can also be avoided.

These and other features, aspects and advantages of the present invention will become better understood with regard to the following description, appended claims, and accompanying drawings.

DETAILED DESCRIPTION OF THE EMBODIMENTS

The invention is illustrated with embodiments, and the same symbols denote the same or similar elements, components or steps.

Figure 1:
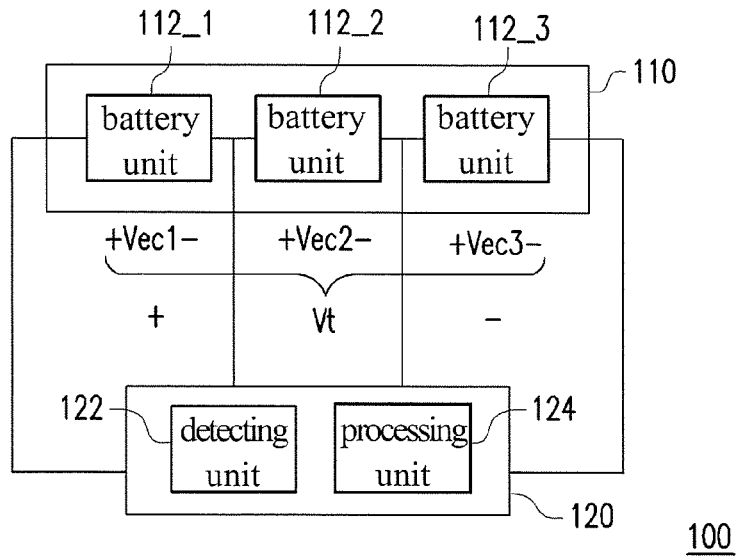
FIG. 1 is a schematic diagram showing a battery module in an embodiment.

FIG. 1 is a schematic diagram showing a battery module in an embodiment. Please refer to FIG. 1, a battery module 100 in the embodiment includes a rechargeable battery 110 and an overcharge protection device 120. In the embodiment, the rechargeable battery 110, such as a lithium battery, may include multiple battery units which are connected to each other in series (in the embodiment, the rechargeable battery 110 includes three battery units 112_1 to 112_3, which is not limited herein). The overcharge protection device 120 may be a micro-controller unit (MCU), a batter management unit (BMU) or other control circuits which include a logic calculating and controlling function, which is not limited herein.

Figure 2:
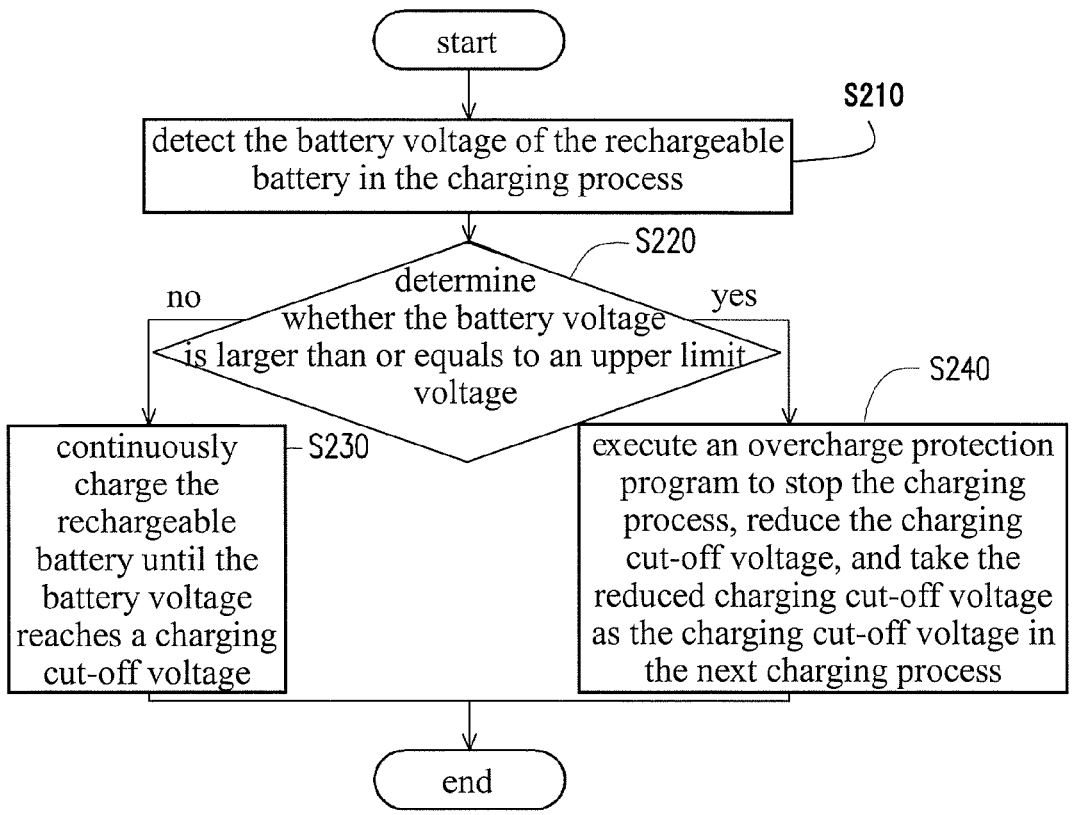
FIG. 2 is a flow chart showing an overcharge protecting method in an embodiment.

In detail, the overcharge protection device 120 may include a detecting unit 122 and a processing unit 124. The detecting unit 122 detects a battery voltage of the rechargeable battery 110 in a charging process. When an overcharge of the rechargeable battery 110 occurs, the processing unit 124 executes an overcharge protecting method shown in FIG. 2 according to a voltage detecting result of the detecting unit 122. FIG. 2 is a flow chart showing an overcharge protecting method in an embodiment.

Please refer to FIG. 1 and FIG. 2 at the same time, in the overcharge protecting method, after a charging process of the rechargeable battery 110 starts, the battery voltage of the rechargeable battery 110 in the charging process is detected or monitored (step S210), and it is determined that whether the battery voltage is larger than or equals to an default upper limit voltage (the upper limit voltage is a predetermined voltage which can enable an overcharge protection, and it is represented by "the upper limit voltage" in the following) (step S220). The battery voltage may be a voltage Vec1, Vec2 or Vec3 across each battery unit 112_1 to 112_3, or a voltage Vt across the rechargeable battery 110 (which equals to a series voltage of Vec1 to Vec3), which is not limited herein.

In the step S220, if it is determined that the battery voltage is smaller than the upper limit voltage, it means the rechargeable battery 110 is at a normal charge state, and the rechargeable battery 110 is continuously charged until the battery voltage reaches a charging cut-off voltage (which is a predetermined voltage that indicates the charging of the rechargeable battery is finished). Then, the charging process ends (step S230).

On the other hand, in the step S220, if it is determined that the battery voltage is larger than or equals to the upper limit voltage, it means the battery voltage rises unexpectedly and abnormally (which means an overcharge occurs) due to the degradation of the rechargeable battery 110. Consequently, an overcharge protection program is further executed to stop the charging process, reduce the charging cut-off voltage, and take the reduced charging cut-off voltage as the charging cut-off voltage in the next charging process (step S240).

More specifically, in the embodiment, once the overcharge of the rechargeable battery 110 occurs in the charging process, the processing unit 124 reduces the charging cut-off voltage by one order (each order of the reduced unit voltage may be 0.1V). In other words, if the overcharge of the rechargeable battery 110 occurs frequently in the charging process, the processing unit 124 of the overcharge protection device 120 gradually reduces the charging cut-off voltage in every charging process until the overcharge of the rechargeable battery 110 does not occur (which means the battery voltage is smaller than the upper limit voltage), and the reduced charging cut-off voltage is taken as a setting basis in the subsequent charging processes. Moreover, if the overcharge of the rechargeable battery 110 occurs again in the subsequent charging process, the charging cut-off voltage is reduced again according to the steps of the overcharge protecting method in the embodiment.

The steps can by executed by the processing unit 124 via a specific hardware configuration or software, which is not limited herein.

The charging cut-off voltage can be set according to each battery unit 112_1 to 112_3 or the whole rechargeable battery 110, which is not limited herein. For example, taking the lithium battery as an example, the charging cut-off voltage of each battery unit 112_1 to 112_3 may be 4.2V. If the charging cut-off voltage is set according to the whole rechargeable battery 110, the charging cut-off voltage may be 12.6V. Furthermore, the upper limit voltage in the steps may be selected according to the features of the rechargeable battery 110, taking the lithium battery as an example, the upper limit voltage of each battery unit 112_1 to 112_3 may be 4.3V. The upper limit voltage of the whole rechargeable battery 110 may be 12.9V, which is not limited herein.

Figure 3A:
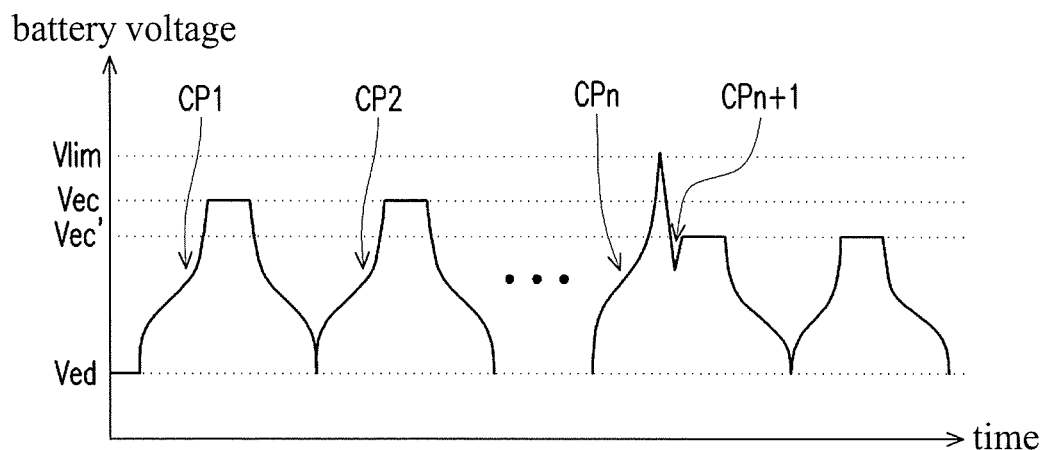
FIG. 3A and FIG. 3B are schematic diagrams showing charging processes of a rechargeable battery in different embodiments.
Figure 3B:
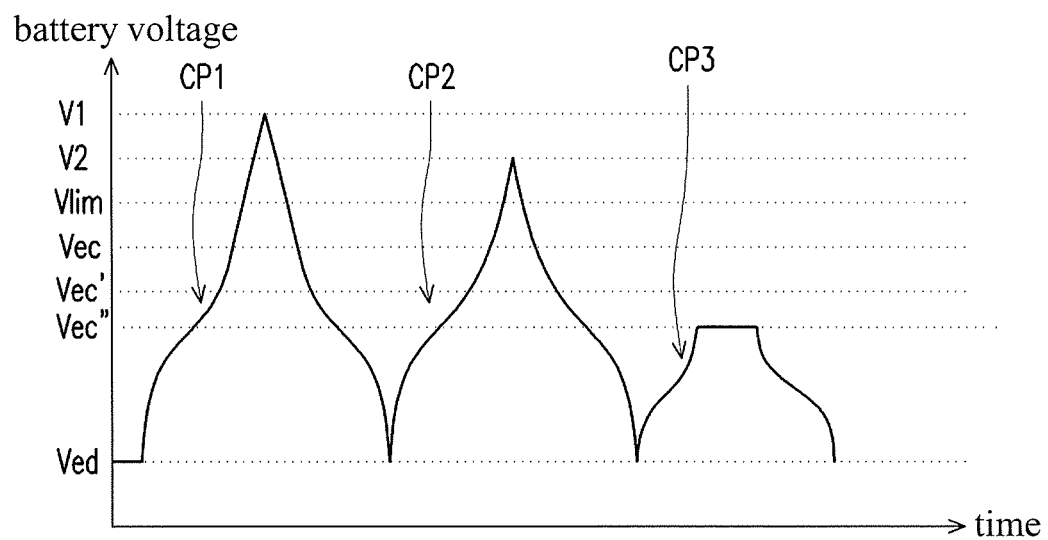

The steps of the charging process in FIG. 2 are illustrated with FIG. 3A and FIG. 3B in the following. FIG. 3A and FIG. 3B are schematic diagrams showing the charging processes of the rechargeable battery in different embodiments.

Please refer to FIG. 2 and FIG. 3A, when the rechargeable battery is in a normal charging process, such as a first charging process CP1, the rechargeable battery is gradually charged from a discharge cut-off voltage Ved to the predetermined charging cut-off voltage Vec (such as 4.2V), and when the battery voltage reaches the charging cut-off voltage Vec, the charging process is ended. At this state, the overcharge protection device determines that the overcharge of the rechargeable battery does not occur (which means the battery voltage is smaller than the upper limit voltage Vlim, such as 4.3V). Thus, in the next charging process CP2, the charging protection device still uses the charging cut-off voltage Vec as the predetermined charging cut-off voltage. Furthermore, the overcharge protection device continuously uses the charging cut-off voltage Vec as the predetermined charging cut-off voltage in the subsequent charging process as long as the overcharge of the rechargeable battery does not occur.

On the other hand, when the overcharge protection device determines the overcharge of the rechargeable battery occurs in the Nth charging process CPn (which means the battery voltage is larger than or equals to the upper limit voltage Vlim), the overcharge protection device executes the overcharge protection program stated in the previous embodiment to stop the charging process CPn, and reduces the charging cut-off voltage from Vec to Vec' (such as 4.1V). Thus, in the next charging process CPn+1, the rechargeable battery is charged based on the predetermined charging cut-off voltage Vec'.

In the charging process CPn+1, since the rechargeable battery is based on the charging cut-off voltage Vec' and the overcharge does not occur, the overcharge protection device still takes the charging cut-off voltage Vec' as the predetermined charging cut-off voltage in the charging process CPn+2. The subsequent charging processes can be deduced by analogy.

Please refer to FIG. 2 and FIG. 3B, in the embodiment, the overcharge of the rechargeable battery occurs frequently and the overcharge protection device reduces the charging cut-off voltage for several times in the charging processes.

In detail, in the charging process CP1, the detecting unit of the overcharge protection device detects that the battery voltage continuously increases and reaches a voltage V1 which is larger than the upper limit voltage Vlim. At the moment, the processing unit of the overcharge protection device determines that the overcharge of the rechargeable battery occurs, and the overcharge protection program is executed to stop the charging process CP1 and reduce the charging cut-off voltage Vec to Vec' (such as reducing from 4.2V to 4.1V).

In the next charging process CP2, although the charging cut-off voltage Vec is reduced to Vec', since the overcharge of the rechargeable battery still occurs in the charging process CP2 and the battery voltage continuously increases and reaches a voltage V2 (compared with the voltage V1 in the charging process CP1, the voltage V2 is closer to the upper limit voltage Vlim) which is larger than the upper limit voltage Vlim, the overcharge protection device executes the overcharge protection program again to stop the charging process CP2 and further reduce the charging cut-off voltage Vec' to Vec" (such as reducing from 4.1V to 4.0V).

In the next charging process CP3, since the rechargeable battery is charged based on the charging cut-off voltage Vec", it would not be charged to a voltage larger than the upper limit voltage Vlim. When the battery voltage reaches the charging cut-off voltage Vec", the overcharge protection device determines charging of the rechargeable battery is finished, and the overcharge does not occur, so the charging process CP3 ends normally. Then, the overcharge protection device takes the charging cut-off voltage Vec" as the predetermined charging cut-off voltage in every charging process unless the overcharge of the rechargeable battery occurs again.

As stated above, in the overcharge protecting method of the embodiment, the overcharge protection device sets the charging cut-off voltage in every charging process based on the final charging cut-off voltage in the previous charging process. In other words, once the overcharge of the rechargeable battery occurs, the overcharge protection device adjusts the predetermined charging cut-off voltage according to the final charging cut-off voltage in the previous charging process, so as to avoid the overcharge in the next charging process.

Figure 4:
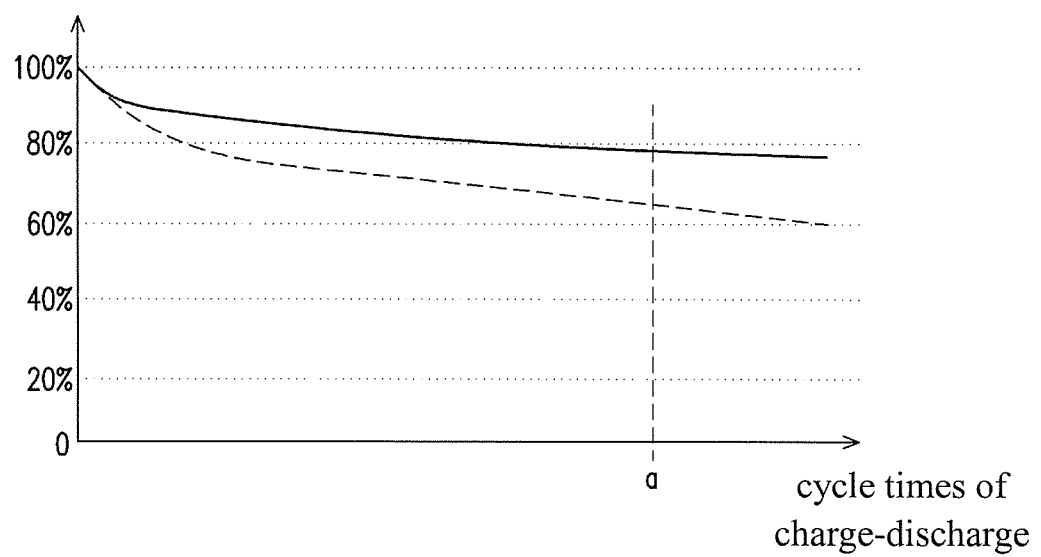
FIG. 4 is a schematic diagram showing a comparing of a rechargeable battery service life using an overcharge protecting method and a conventional charging method.

The overcharge protecting method can effectively reduce the chance of overcharging the rechargeable battery, and it can also extend a service life of the rechargeable battery. FIG. 4 is a schematic diagram showing a comparing of the rechargeable battery service life using the overcharge protecting method and a conventional charging method.

As shown in FIG. 4, the vertical axis represents a ratio of a practical discharge capacity of the rechargeable battery and a discharge capacity of the first time. For example, "100%" means that the practical discharge capacity of the rechargeable battery equals to the discharge capacity of the rechargeable battery at the first time, and "80%" means that the practical discharge capacity of the rechargeable battery is 80% of the discharge capacity of the rechargeable battery at the first time. The horizontal axis represents a cycle times of charge-discharge.

The curve in a full line shows the features of the rechargeable battery applying the overcharge protecting method, and the curve in a dotted line shows the features of the rechargeable battery applying a conventional charging method (that is, the charging cut-off voltage is constant). As shown in the figure, after a same cycle times of charge-discharge, the rechargeable battery applying the overcharge protecting method has a higher practical battery capacity. For example, after several charge-discharge cycles, the rechargeable battery in the embodiment still has about 80% practical battery capacity, and the rechargeable battery applying the conventional charging method only has about 60% practical battery capacity. Thus, the rechargeable battery applying the overcharge protecting method has a longer service life.

Figure 5A:
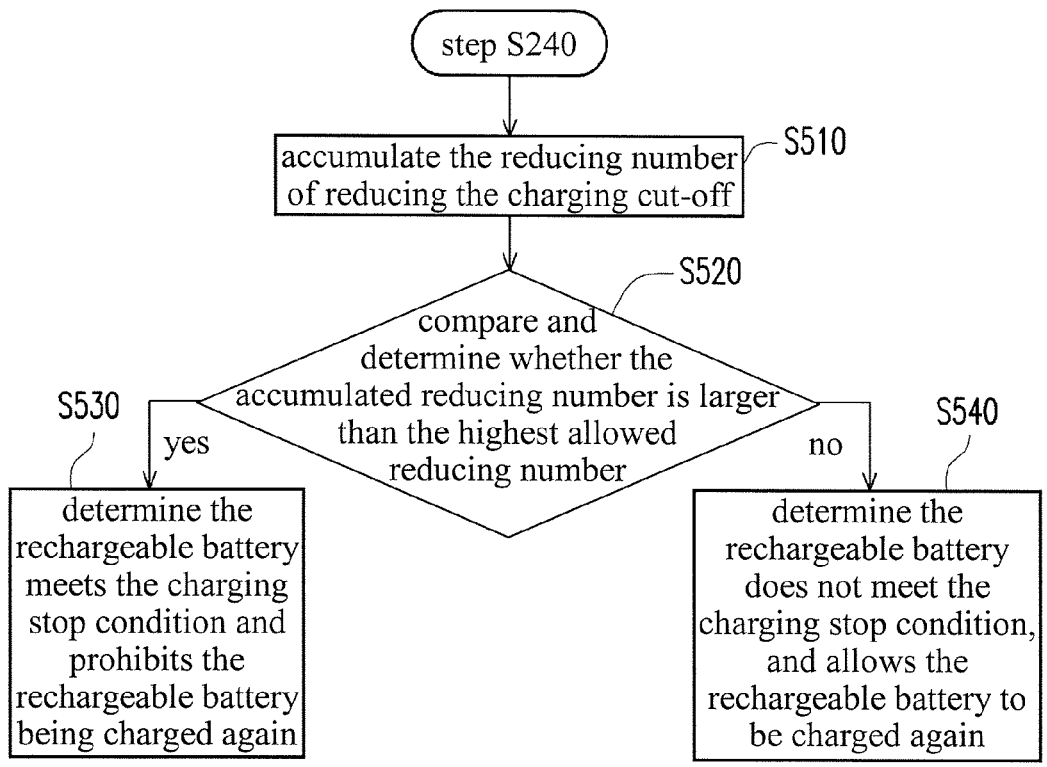
FIG. 5A and FIG. 5B are flow charts showing the overcharge protecting method in FIG. 2 in different embodiments.
Figure 5B:
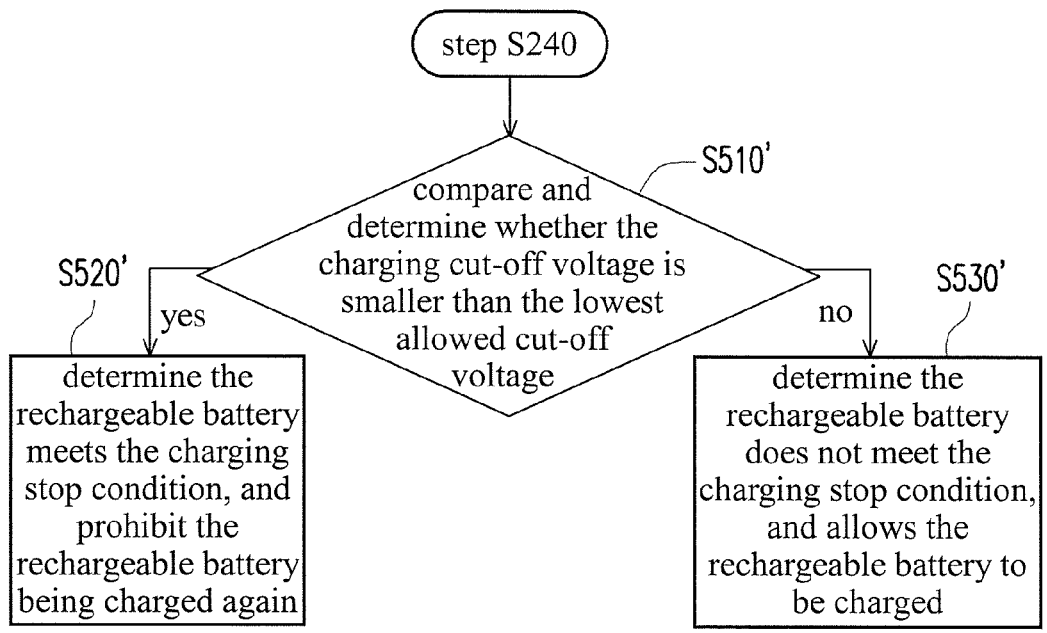

In the overcharge protecting method, whether the charging process should be stopped can be determined according to whether the battery voltage is larger than the upper limit voltage Vlim, and it can also be determined according to whether the rechargeable battery meets a stop charging condition and is at a normal charge-discharge state during the overcharge protection program. Furthermore, a secondary protection function may be enabled to prohibit the rechargeable battery being charged or discharged. FIG. 5A and FIG. 5B are flow charts showing the stop charging conditions of the overcharge protecting method in FIG. 2 in different embodiments.

As shown in FIG. 5A, in the embodiment, after the overcharge protection program is executed (the step S240), the overcharge protection device accumulates the reducing number of reducing the charging cut-off voltage (step S510), and compares the accumulated reducing number and a predetermined highest allowed reducing number (which can be set by a programmer) to determine whether the accumulated reducing number is larger than the highest allowed reducing number (step S520). If yes (which means the reducing number is larger than the highest allowed reducing number), the overcharge protection device determines the rechargeable battery meets the stop charging condition, and prohibits the rechargeable battery being charged again (step S530). On the contrary, if no (which means the reducing number is smaller or equals to the highest allowed reducing number), the overcharge protection device determines the rechargeable battery does not meet the stop charging condition, and allows the rechargeable battery to be charged again (step S540). In other words, the stop charging condition in the embodiment is the reducing number of reducing the charging cut-off voltage.

For example, the predetermined highest allowed reducing number is 10, when the accumulated number of reducing the charging cut-off voltage is larger than 10 and the overcharge of the rechargeable battery still occurs, the overcharge protection device determines the rechargeable battery may be degraded and cannot be charged and discharge normally. Then, the secondary protection function is enabled to prohibit the rechargeable battery being charged or discharged again. The secondary protection function may be a fuse in the rechargeable battery is burnt out to prohibit the charge-discharge of the rechargeable battery.

In another embodiment, as shown in FIG. 5B, after the overcharge protection program is executed (S240), the overcharge protection device compares the charging cut-off voltage with a predetermined lowest allowed cut-off voltage, and determines whether the charging cut-off voltage is smaller than the lowest allowed cut-off voltage (step S510'). If yes (which means the charging cut-off voltage is smaller than the lowest allowed cut-off voltage), the overcharge protection device determines the rechargeable battery meets the stop charging condition, and prohibits the charging of the rechargeable battery (step S520'). On the contrary, if no (which means the charging cut-off voltage is larger than or equals to the lowest allowed cut-off voltage), the overcharge protection device determines the rechargeable battery does not meet the stop charging condition, and allows the rechargeable battery to be charged (step S530'). In other words, in the embodiment, the stop charging condition is the value of the charging cut-off voltage.

For example, the predetermined lowest allowed cut-off voltage is 3.5V. When the overcharge protection device reduces the charging cut-off voltage to be lower than 3.5V and the overcharge of the rechargeable battery still occurs, the overcharge protection device determines that the rechargeable battery may be degraded and cannot be charged and discharge normally. Thus, the secondary protection function is enabled to prohibit the charge-discharge of the rechargeable battery.

Although the present invention has been described in considerable detail with reference to certain preferred embodiments thereof, the disclosure is not for limiting the scope. Persons having ordinary skill in the art may make various modifications and changes without departing from the scope. Therefore, the scope of the appended claims should not be limited to the description of the preferred embodiments described above.

What is claimed is:

1. An overcharge protecting method for a rechargeable battery, comprising following steps:
   detecting a battery voltage of the rechargeable battery in a charging process;
   determining whether the battery voltage is larger than or equals to an upper limit voltage;
   if no, continuously charging the rechargeable battery until the battery voltage reaches a charging cut-off voltage and then the charging process is ended; and
   if yes, stopping the charging process, reducing a value of the charging cut-off voltage and using the reduced charging cut-off voltage as the charging cut-off voltage in the next charging process.

2. The overcharge protecting method for the rechargeable battery according to claim 1, wherein the charging cut-off voltage in each charging process is based on the final charging cut-off voltage in the previous charging process.

3. The overcharge protecting method for the rechargeable battery according to claim 1, wherein the step of detecting the battery voltage of the rechargeable battery in the charging process further includes:
   determining whether the rechargeable battery meets a stop charging condition; and
   if yes, ending the charging process.

4. The overcharge protecting method for the rechargeable battery according to claim 3, wherein the step of determining whether the rechargeable battery meets the stop charging condition includes:
   accumulating a reducing number of reducing the charging cut-off voltage;
   comparing the reducing number and a highest allowed reducing number; and
   determining the rechargeable battery meets the stop charging condition when the reducing number is larger than the highest allowed reducing number.

5. The overcharge protecting method for the rechargeable battery according to claim 3, wherein the step of determining whether the rechargeable battery meets the stop charging condition includes:
   comparing the charging cut-off voltage and a lowest allowed cut-off voltage; and
   determining that the rechargeable battery meets the stop charging condition when the charging cut-off voltage is smaller than the lowest allowed cut-off voltage.

6. The overcharge protecting method for the rechargeable battery according to claim 3, wherein when the stop charging condition is met, the overcharge protecting method further includes:
   enabling a secondary protection function to prohibit the rechargeable battery being charged or discharged again.

7. A battery module capable of being charged and discharge repeatedly, comprising:
   a rechargeable battery; and
   an overcharge protection device, wherein the overcharge protection device includes:
   a detecting unit detecting a battery voltage of the rechargeable battery in a charging process; and
   a processing unit coupled to the detecting unit, wherein the processing unit determines whether the battery voltage is larger than or equals to an upper limit voltage in the charging process; when the processing unit determines the battery voltage is smaller than the upper limit voltage, the rechargeable battery is continuously charged until the battery voltage reaches a charging cut-off voltage and the charging process is ended; when the processing unit determines the battery voltage is larger than or equals to the upper limit voltage, the processing unit stops the charging process and reduces the value of the charging cut-off voltage, and the processing unit takes the reduced charging cut-off voltage as the charging cut-off voltage in the next charging process.

8. The battery module according to claim 7, wherein in each charging process, the processing unit sets the reduced charging cut-off voltage in the previous charging process as the charging cut-off voltage.

9. The battery module according to claim 7, wherein the processing unit determines whether the rechargeable battery meets a stop charging condition, when the processing unit determines the rechargeable battery meets the stop charging condition, the charging process is ended.

10. The battery module according to claim 7, wherein the processing unit accumulates a reducing number of reducing the charging cut-off voltage, and determines whether the rechargeable battery meets a stop charging condition according to a result of comparing the reducing number and a highest allowed reducing number, and when the reducing number is larger than the highest allowed reducing number, the processing unit determines the rechargeable battery meets the stop charging condition.

11. The battery module according to claim 7, wherein the processing unit determines whether the rechargeable battery meets a stop charging condition according to a result of comparing the charging cut-off voltage and a lowest allowed cut-off voltage, and when the charging cut-off voltage is smaller than the lowest allowed cut-off voltage, the processing unit determines the rechargeable battery meets the stop charging condition.

12. The battery module according to claim 7, wherein when the processing unit determines the rechargeable battery meets a stop charging condition, the processing unit enables a secondary protection function to prohibit the rechargeable battery being charged or discharged again.

* * * * *